(12) United States Patent
Reckelhoff (10) Patent No.: US 8,180,485 B2
(45) Date of Patent: May 15, 2012

(54) MEDICATION DISPENSING CART (75) Inventor: Ray Reckelhoff, Camden, SC (US)

(73) Assignee: Omnicell, Inc., Mountain View, CA (US)

( * ) Notice: Subject to any disclaimer, the term of this patent is extended or adjusted under 35 U.S.C. 154(b) by 735 days.

(21) Appl. No.: 12/278,263

(22) PCT Filed: Feb. 12, 2007

(86) PCT No.: PCT/US2007/003765
§ 371 (c)(1),
(2), (4) Date: Mar. 11, 2009

(87) PCT Pub. No.: WO2007/095222
PCT Pub. Date: Aug. 23, 2007

(65) Prior Publication Data
US 2010/0004780 A1 Jan. 7, 2010

Related U.S. Application Data (60) Provisional application No. 60/772,416, filed on Feb. 11, 2006.

(51) Int. Cl.
G06F 17/00 (2006.01)
(52) U.S. Cl. .................. 700/242; 700/237; 700/243
(58) Field of Classification Search .............. 700/237, 700/242, 243
See application file for complete search history.

(56) References Cited

U.S. PATENT DOCUMENTS

| 4,368,867 | A | 1/1983 | Pendleton |
|---|---|---|---|
| 4,372,515 | A | 2/1983 | Noonan |
| 4,471,931 | A | 9/1984 | Covey |
| D279,007 | S | 5/1985 | Empson |
| 4,556,189 | A | 12/1985 | Kirpluk |
| 4,561,620 | A | 12/1985 | Goetz |
| 4,575,033 | A | 3/1986 | Henneberg |
| 4,589,621 | A | 5/1986 | Hunt |
| 4,616,218 | A | 10/1986 | Bailey |
| 4,640,199 | A | 2/1987 | Zigman |
| 4,645,153 | A | 2/1987 | Granzow |
| D289,873 | S | 5/1987 | Gemmell |
| D293,382 | S | 12/1987 | Ichikawa |
| 4,717,112 | A | 1/1988 | Pirkle |
| 4,726,633 | A | 2/1988 | Noble |
| 4,729,533 | A | 3/1988 | Hillary |

(Continued)

FOREIGN PATENT DOCUMENTS

DE 29506433 U1 10/1995

(Continued)

Primary Examiner — Timothy Waggoner
(74) Attorney, Agent, or Firm — Kilpatrick Townsend & Stockton LLP (57) ABSTRACT A medication dispensing cart (10) having a computer and monitor (12), a work surface (16) with pull out keyboard (18), and plural drawers (30) arranged as a vertical series of cassettes that can be added as needed. The battery powered device uses software and pass codes for controlling access to each drawer, and requires a second pass code for any drawer designated to contain narcotics. Records can be kept of who dispenses what medication and when for each cart in a system of carts. The cart in the system is in wireless communication with a system administrator. Emails alerting the system administrator of low battery power, of a cart switching to off, of an attempted break-in, and of inventory and usage data are sent automatically by email.

36 Claims, 7 Drawing Sheets

U.S. PATENT DOCUMENTS

| | | |
|---|---|---|
| D295,415 S | 4/1988 | Thies |
| 4,769,634 A | 9/1988 | Killian |
| 4,834,329 A | 5/1989 | Delapp |
| 4,836,478 A | 6/1989 | Sweere |
| 4,836,486 A | 6/1989 | Vossoughi |
| 4,852,500 A | 8/1989 | Ryburg |
| 4,918,841 A | 4/1990 | Turner |
| 4,919,387 A | 4/1990 | Sampson |
| D310,358 S | 9/1990 | Nuttall |
| 4,967,928 A | 11/1990 | Carter |
| D312,630 S | 12/1990 | Esslinger |
| 4,989,291 A | 2/1991 | Parent |
| D317,912 S | 7/1991 | Takai |
| D319,405 S | 8/1991 | Brawne |
| 5,041,770 A | 8/1991 | Seiler |
| D326,847 S | 6/1992 | Savio |
| 5,174,223 A | 12/1992 | Nagy |
| D337,104 S | 7/1993 | Orchard |
| D339,796 S | 9/1993 | Goodner |
| 5,277,392 A | 1/1994 | Rossman |
| 5,287,815 A | 2/1994 | Gross |
| D344,933 S | 3/1994 | Wiseman |
| 5,321,579 A | 6/1994 | Brown |
| D348,449 S | 7/1994 | Rodd |
| D349,489 S | 8/1994 | Wang |
| 5,362,025 A | 11/1994 | Trom |
| D354,052 S | 1/1995 | Imai |
| D354,952 S | 1/1995 | Rodd |
| D357,468 S | 4/1995 | Rodd |
| 5,437,235 A | 8/1995 | Randolph |
| 5,442,512 A | 8/1995 | Bradbury |
| 5,473,997 A | 12/1995 | Solomon |
| 5,522,323 A | 6/1996 | Richard |
| 5,536,084 A | 7/1996 | Curtis |
| 5,630,566 A | 5/1997 | Case |
| 5,687,717 A | 11/1997 | Halpern |
| 5,694,199 A | 12/1997 | Rodriguez |
| D393,382 S | 4/1998 | Rutter |
| 5,772,637 A | 6/1998 | Heinzmann |
| 5,842,672 A | 12/1998 | Sweere |
| 5,868,079 A | 2/1999 | Charny |
| 6,061,104 A | 5/2000 | Evanicky |
| 6,085,972 A | 7/2000 | Wright |
| 6,098,936 A | 8/2000 | Birrell |
| 6,170,929 B1 | 1/2001 | Wilson et al. |
| 6,175,779 B1 * | 1/2001 | Barrett .................. 700/242 |
| 6,269,753 B1 | 8/2001 | Roddan |
| 6,298,794 B1 | 10/2001 | Brown |
| 6,339,732 B1 | 1/2002 | Phoon et al. |
| 6,394,402 B2 | 5/2002 | Coonan |
| 6,435,109 B1 | 8/2002 | Dell |
| 6,493,220 B1 * | 12/2002 | Clark et al. ............. 361/679.41 |
| 6,604,019 B2 * | 8/2003 | Ahlin et al. .................... 700/231 |
| 6,721,178 B1 | 4/2004 | Clark |
| 6,775,591 B1 | 8/2004 | Shoenfeld |
| 6,996,455 B2 * | 2/2006 | Eggenberger et al. ........ 700/231 |
| 7,009,840 B2 | 3/2006 | Clark |
| 7,154,397 B2 * | 12/2006 | Zerhusen et al. ........ 361/679.21 |
| 7,747,347 B2 * | 6/2010 | Park, IV ..................... 700/243 |
| 2006/0125356 A1 * | 6/2006 | Meek et al. .................. 312/215 |

FOREIGN PATENT DOCUMENTS

| | | |
|---|---|---|
| DE | 19536664 A1 | 4/1997 |
| DE | 19642425 A1 | 4/1998 |
| DE | 19650100 A1 | 6/1998 |
| EP | 0145410 A2 | 6/1985 |
| EP | 0321137 A2 | 6/1989 |
| EP | 0796575 A1 | 9/1997 |
| JP | 5-151510 | 6/1993 |
| JP | 9-13939 | 1/1997 |
| JP | 9-262137 | 10/1997 |
| JP | 10-146224 A | 6/1998 |
| JP | 11-127976 A | 5/1999 |
| WO | WO97/46824 | 12/1997 |

* cited by examiner

MEDICATION DISPENSING CART

BACKGROUND OF THE INVENTION

The present invention relates to dispensing medication to patients in hospitals and nursing homes.

In the health care industry, an important component of patent care is medication. Medications, in the form of pills, capsules and liquids, are given to patients to relieve pain, to prevent or eliminate infections, and to treat illnesses and disease. Oftentimes the medications are given in doses that ate repeated at intervals during the day and may be part of a regimen that takes place over several days or even an extended period of time for chronic illness. Medications may have a powerful effect on the body. Some medications should not be taken with other medications or are carefully controlled because of their impact on the patient if too much is administered or because they are subject to abuse by others.

In addition, if the wrong medication is given to a patient, or if the correct medication is given but in too large a dose or too frequently, harm may result. Accordingly, it is important to doctors, nurses and the staff and management of hospitals and nursing homes to make sure their patients take all prescribed medications and only the prescribed medication and to take them in accordance with their prescriptions. Usually, administrative controls and paper records, sometimes augmented by security measures, are used to achieve these objectives.

However, there remains a need for better ways to dispense medications in a controlled manner.

SUMMARY OF THE INVENTION

The following presents a simplified summary of the invention in order to provide a basic understanding of some aspects of the invention. This summary is not an extensive overview of the invention. It is not intended to identify key or critical elements of the invention or to delineate the scope of the invention. Its sole purpose is to present some concepts of the invention in a simplified form as a prelude to the more detailed description that is presented later.

According to its major aspects and briefly recited, the present invention is a cart designed for dispensing medication. The cart carries a computer for keeping track of who dispenses what type of medication, when it is dispensed, and that corroborates dispensing information automatically.

The present cart includes a computer with wireless network access and a monitor, a power system having a battery pack to provide power to the computer and monitor, a cassette drawer system having one or more cassette drawers for holding medications, and a security system. Generally, the cassette drawer system, the power system and the security system are software controlled. Access to the cassette drawers is by pass code entry via the computer keyboard or a key override. Each cart user has a different code and only those having valid pass codes or keys can access the drawers. Particular medications, such as narcotics, require a second pass code or second key.

The installation and use of the drawers is sensed by the computer so that it can record who accessed which cassette drawer and when. The use of the computer to track the dispensing of medications enables the cart administrator to compile this information and thereby confirm the medications were given by the cart users as prescribed.

An important feature of the present invention is the use of email from the computer over a wireless network linking all other carts on a system. This feature allows the computer on each cart to keep an administrator informed of the status of each cart, such as the condition of the battery and the use of the cart. It also informs the administrator if there has been an attempt to open a drawer by force.

Another important feature is the cassette drawer system. The drawer system allows additional drawers to be added or drawers to be removed. Drawers that have been added are automatically sensed by the computer and can then be opened only by those who have been given a code that permits access. Once a drawer has been added, it cannot be removed unless it is first opened.

Still another important feature is the use of software to control access. The computer keyboard allows entry of pass codes by users and unlocks only the drawer they wish to access. No separate key pad or lock and key system is needed.

Yet another feature is the use of software to control the raising and lowering of the computer monitor and work station. An electrical switch that is connected to the power system enables a user to adjust the height of the cart work station so that use of the cart can be made both in a standing and seated position.

Still another feature of the present invention is the use of a power system that can be charged independently from the cart. The use of an encapsulated, self-contained power system and battery enables the user to charge the battery in smaller, more confined areas. Furthermore, a user can simply exchange a low charge power system for a fully charged power system without having to remove and replace the internal battery.

These and other features and their advantages will be apparent to those skilled in the art of dispensing medications to patients from a careful reading of the Detailed Description of Preferred Embodiments accompanied by the following drawings.

DETAILED DESCRIPTION OF THE INVENTION

Figure 1:
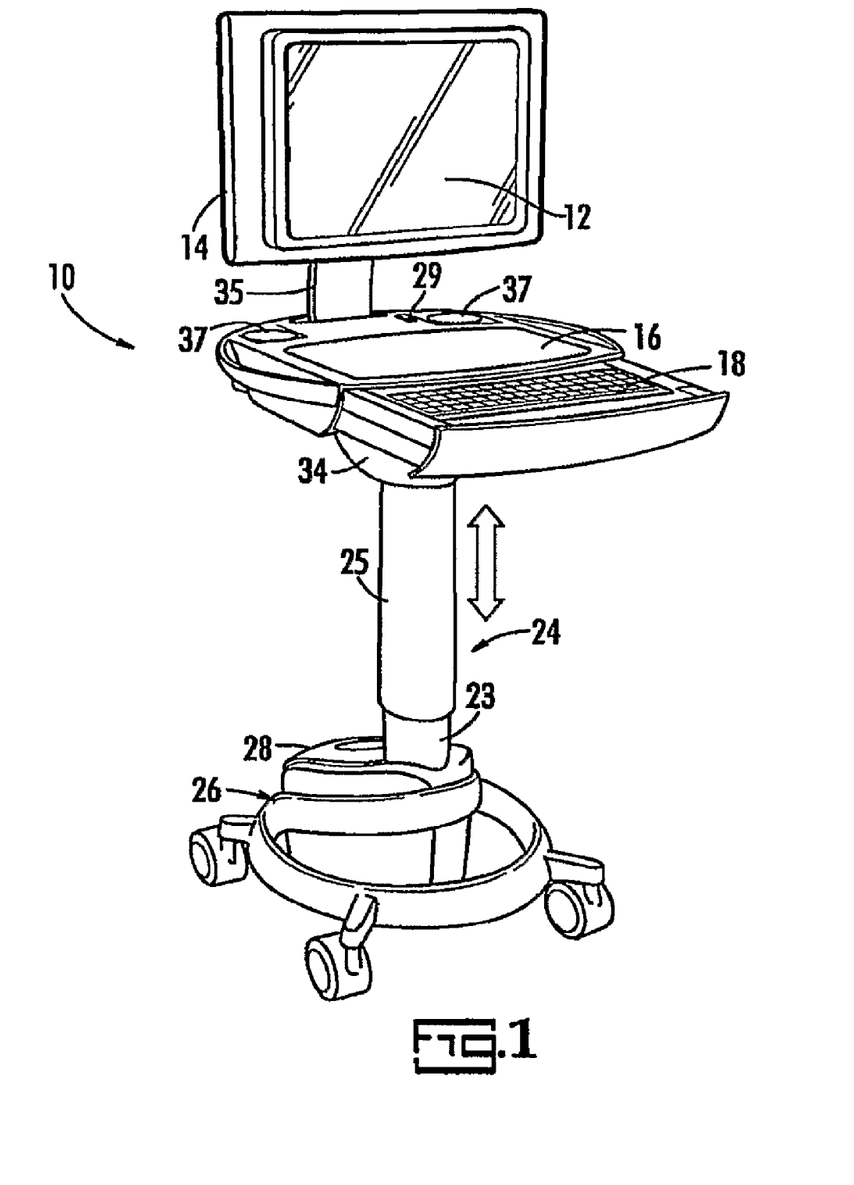
FIG. 1 is a perspective view of one embodiment of a medication dispensing cart according to the invention.
Figure 2:
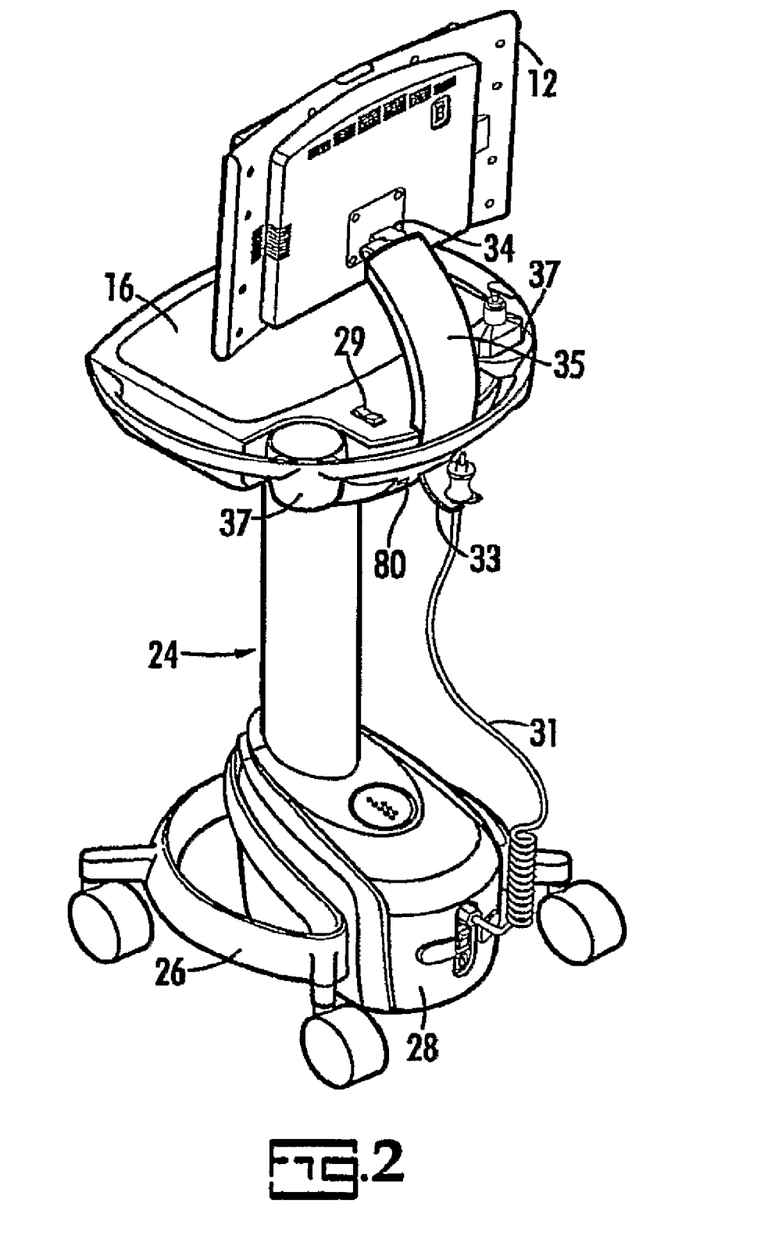
FIG. 2 is a rear view of the medication dispensing cart of FIG. 1.
Figure 3:
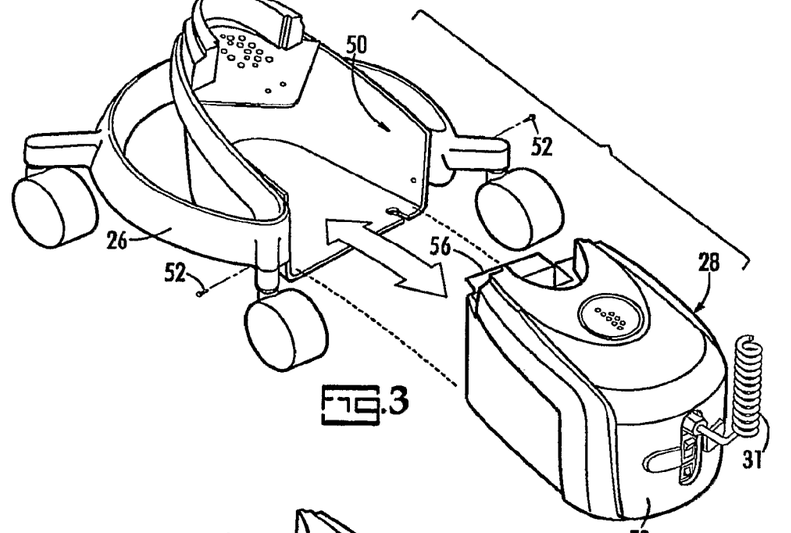
FIG. 3 is an exploded perspective view of a base of the medication dispensing cart of FIG. 1.

FIG. 1 is a perspective illustration of a medication dispensing cart, according to a preferred embodiment of the present invention;

FIG. 2 illustrates a rear, perspective view of a medication dispensing cart according to a preferred embodiment of the present invention;

FIG. 3 is a detailed, exploded, perspective view of the base of a medication dispensing cart, showing the battery in its cover being separated from the battery bracket on indicated in FIG. 1 by reference number 10, includes a computer/monitor 12, preferably with both a computer and a monitor in one unit with the computer behind the monitor and in the same housing 14. Cart 10 also has a work surface 16 with a slide out keyboard 18. There is no security keypad; the keyboard's keypad serves for entry of codes to permit access. Work surface 16 is mounted on top of a mast 24 carried in turn by a rolling base 26. Work surface 16 can optionally include holders for storing items, such as antibacterial lotions and drinks, which the user may need when making rounds with the cart 10.

Referring to FIG. 2, there is illustrated a rear view of the present cart 10 showing computer/monitor 12, work surface 16, mast 24, and a power system 28, which is carried by rolling base 26. Work surface 16 can further include hidden USB port 80 for use if additional electronic devices, such as scanners, need to be employed. Computer/monitor 12 is attached to mast 24 or underneath the work surface through a mount 35 so that the entire top area of the work surface 16 is available to the user. Computer/monitor 12 is mounted using a tiltable bracket 34 so that the angle of viewing computer/monitor 12 can be adjusted to suit the particular user. A clear hard covering is applied over the monitor portion of computer/monitor 12 in order to make computer/monitor less susceptible to scratches and impact. Preferably the covering is about a $1/8^{th}$ inch thick and made of acrylic polymeric plastic or other suitable plastic polymer.

Mast 24 is vertically adjustable so that the user can work seated or standing and users of different heights can work comfortably. Preferably, mast 24 is electronically adjustable by pressing a button 29 rather than by turning a hand crank or other mechanical elevating mechanism. As shown in FIG. 1, the mast 24 is telescoped, with an outer mast member 25 dimensioned to receive an inner mast member 23. This arrangement enables the raising and lowering of the computer/monitor 12 and work surface 16. The raising and lowering of the mast 24 can be controlled by an electrical switch 29 that is connected to the power system 28 and mechanical means (not shown), such as a screw/nut drive system that utilizes a number of small balls (ball screw). In operation, a user would press the button 29 in one direction, such as forward, to activate the electrical switch 29 to lower the mast 24, and in another direction, such as backward, to activate the electrical switch 29 to raise the mast 24. The electrical switch 29 provides input to the power system 28, which controls the raising and lowering of the mast 24 through an actuator connected to the mechanical means. Alternatively, the power system can also include a weight sensor connected to the actuator that can be used to override the raising and lowering of mast 24 based on the weight of the work surface 16 and computer/monitor 12. For example, if the combined weight of the work surface 16 and computer/moniter 12 exceeds a preset, desired weight, the actuator will be tripped, and the mast 24 will no longer be moveable through the use of the button 29.

Figure 4:
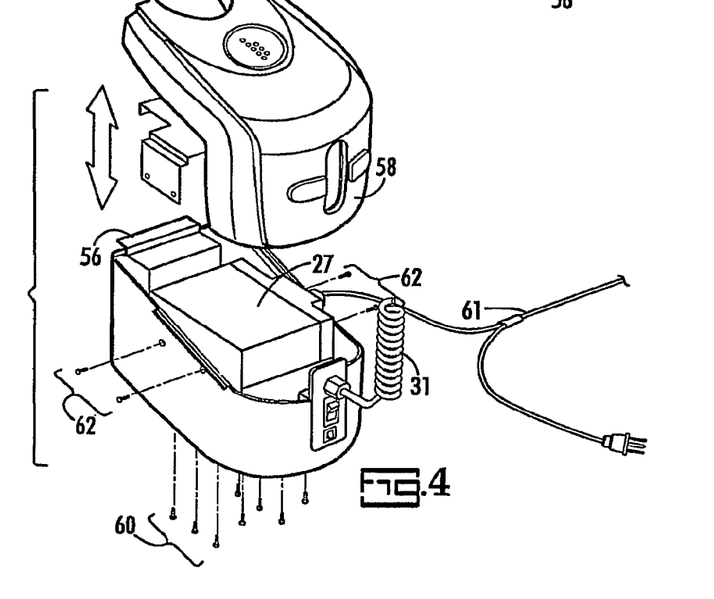
FIG. 4 is a detailed view of a power system of the dispensing cart of FIG. 1.

Power system 28 is illustrated in further detail in FIGS. 3-4. As shown, power system 28, which is connected through mast 24 to computer/monitor 12, includes a power system controller (not shown) and a battery 27 that is carried in a battery bracket 50 held in rolling base 26. As discussed, the battery 27 can be charged in combination with the cart 10 or independently of the cart 10, through a power cord 31. Thus, work surface 16 further includes a power cord 31 plug rest 33 (shown in FIG. 2) for conveniently storing the power cord 31 when the cart 10 is being moved or is not in the vicinity of a power source. Battery 27 can be fixed to battery bracket 50 with a variety of mechanical fasteners. In a preferred embodiment, battery 27 is fixed to battery bracket by two screws 52.

By removing screws 52, battery 27 and its associated electronics can be removed from bracket 50 to expose the wiring connections. Once the wiring connections are disconnected, battery 27 can be lifted free using its handle 56. Battery 24 is still in a cover 58 and may remain in cover 58 during recharging.

In the event battery 27 needs to be replaced altogether, the screws 60 holding battery 27 in its cover 58 are removed, then the battery hold down screws 62 are removed and finally, battery 27 can be disconnected and replaced. It will be clear that having both a battery cover 58 that stays with battery 27 while battery 27 is either in service or being recharged, and which battery 27 and cover 58 can be quickly removed from cart 10, makes it faster and easier to keep fully charged batteries on carts 10.

As discussed, battery 27 can be charged in combination with the cart 10 or independently of the cart 10, through a power cord 31. Thus, work surface 16 further includes a power cord 31 plug rest 33 for conveniently storing the power cord 31 when the cart 10 is being moved or is not in the vicinity of a power source. Additionally, power system 28 can be equipped with an LED indicator to show when the batter 27 is charging and/or fully charged.

Battery 27 is designed to last through at least one shift of eight hours before requiring recharging, preferably about 10 hours. In addition, each battery is connected to the balance of cart 10 using a "Y" electrical connector 61 that permits a second, fully charged battery 27 to be connected (for "hot swapping") to the unused part of the Y connector, and then the first battery 28 can be removed from the battery bracket and disconnected from the Y connector without loss of power, or data, to computer/monitor 12, and the second battery can then be installed into the battery bracket. The connections that hold battery 28 in its bracket are designed for quick release so battery change out takes but a few minutes at most.

Figure 5:
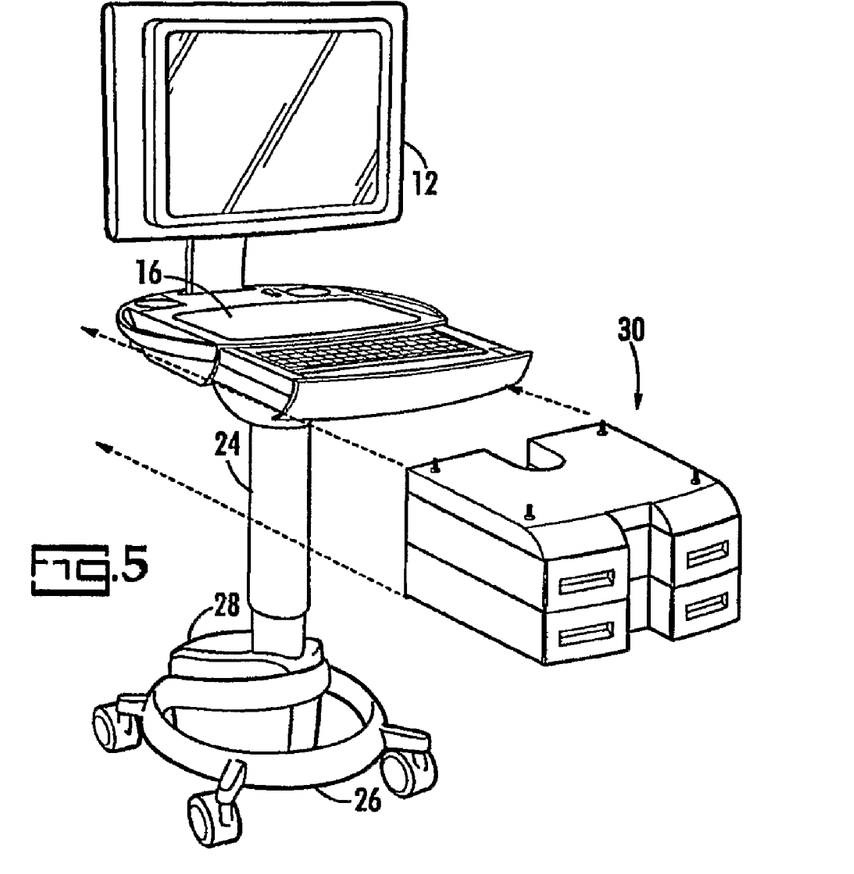
FIG. 5 illustrates a cassette drawer system for a dispensing cart.
Figure 6:
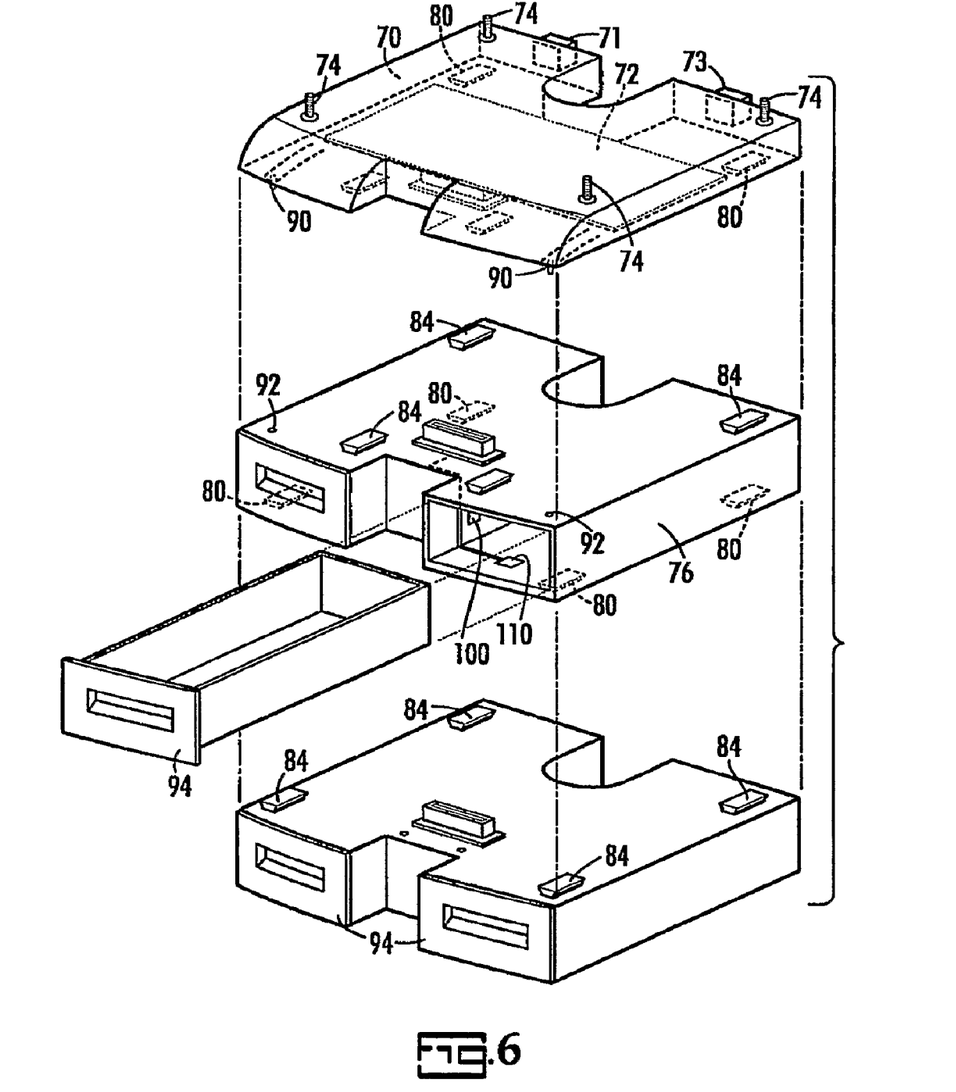
FIG. 6 is an exploded view of the cassette drawer system of FIG. 5.

Referring now to FIG. 5, cart 10 preferably includes a cassette drawer system 30. As illustrated, at least one cassette drawer system 30 can be carried below work surface 16. An exploded, detailed view of the cassette drawer system 30 is shown in FIG. 6. Cassette drawer system 30 is preferably modularized, and includes a cassette drawer manager 70, which houses a cassette drawer controller and interface 72 for monitoring the status and activities of cassette drawers and receiving input for computer/monitor 12. The cassette drawer system 30 is generally connected to work surface 16 and wired to computer/monitor 12. More particularly, the top of cassette drawer manager 70 is bolted to work surface 16. Accordingly, cassette drawer manager 70 includes bolt fasteners 74 along its top surface. Optionally, cassette drawer manager 70 includes a first key override lock 71 and a second key override lock 73. In the event drawers need to be opened, and the cassette drawer system 30 or the computer/monitor 12 system is malfunctioning, a first key from authorized users will override the cassette drawer manager controller 72 to open the drawers containing certain medication. If narcotic medication needs to be accessed, a user must insert both a first key and a second key to open the narcotics-containing drawers.

Beneath cassette drawer manager 70, at least one cassette drawer 76 is latched. Depending on the dimensions of the cassette drawer manager 70 and the cassette drawers, up to four drawers 76 can be added. An added drawer 76 cannot be released without opening the drawer. As soon as a drawer 76 is added, it is sensed by controller of computer/monitor 12 and cannot be opened except by a user with an authorizing pass code.

The latching mechanism between the cassette drawer manager 70 and a cassette drawer 76 will be the same as between a first cassette drawer and a second cassette drawer. This latching mechanism is shown in the expanded detailed drawings in FIG. 6. As between the cassette drawer manger 70 and a first cassette drawer, on the underside of cassette drawer manager 70 are a plurality of dovetail-shaped cutout portions 80 that are dimensioned to receive dovetail-shaped projections 84. Similarly, on the underside of each cassette drawer 76 are a plurality of dovetail-shaped cutout portions 80 that are dimensioned to receive dovetail-shaped projections 84 on every lower cassette drawer 78. In operation, dovetail projections 84 simply slide into dovetail cutouts 80.

Once cassette drawer 76 is seated fully into cassette drawer manager manager 70, spring tabs 90 having pins 91, which have been cut out from the bottom surface of cassette drawer manager 70, are cammed upward as drawer 76 is slid into place, and snap downward into corresponding recesses 92 in the top surface of drawer 76. Pins 91 on spring tabs 90 will hold drawer 76 in place until drawer 76 is opened by an authorized person who can then pull tabs 90 down to release drawer 76 from manager 70. Preferably, once cassette drawer manager 70 and any and all additional cassettes are in place, the cassette drawer manager 70 and the cassette drawers are also electronically connected.

As illustrated, cassette drawer manager 70 and cassette drawer 76 are generally U-shaped to facilitate engagement with the mast 24. Each cassette drawer 76 typically has at least two compartments 94 that are independently lockable through electronic locks 100 and that have corresponding sensors 110. Sensors 110 determine if a drawer is open or closed, including of course when a drawer is left open or not fully closed. A drawer that is opened without authorization causes an alarm to sound and initiates an email to the system administrator. All locks 100 are software controlled rather than by using keys. For example, a lock 100 could include a solenoid actuator connected to a lever and controlled by software. Keys can be lost or stolen or fall into the wrong hands. Furthermore, it is easier to change access pass codes using software than to re-key locks. Computer/monitor 12 can be programmed to lock every drawer unless unlocked by a person with the correct level of authorization who enters the correct pass code via keyboard 18. Access to a compartment 94 containing narcotics requires two pass codes; otherwise one pass code unlocks a compartment 94. Each user has his or her own pass code or codes so the user who accesses each drawer is known by the pass code used, as well as the time and date of the access by that user.

Cart 10 is optionally provided with a plug in scanner for reading medication containers and automatically and accurately loading drawers and the computer database with the correct information about the medications being loaded into each drawer. In this way, the system administrator can have a real time inventory of medications in all carts in its system, knowing exactly what type and how much medication is in each drawer of each cart.

Cassette drawer system 30 also has an optional utility cassette 78, which can be used to store such items as rubber gloves, paper cups, tissues, and so forth. Because a utility cassette 78 need not be secured, cassette drawer manager 70 automatically deactivates sensors 110 and locks 100 of utility cassette drawers 78 that become part of the cassette drawer system 30.

Figure 7:
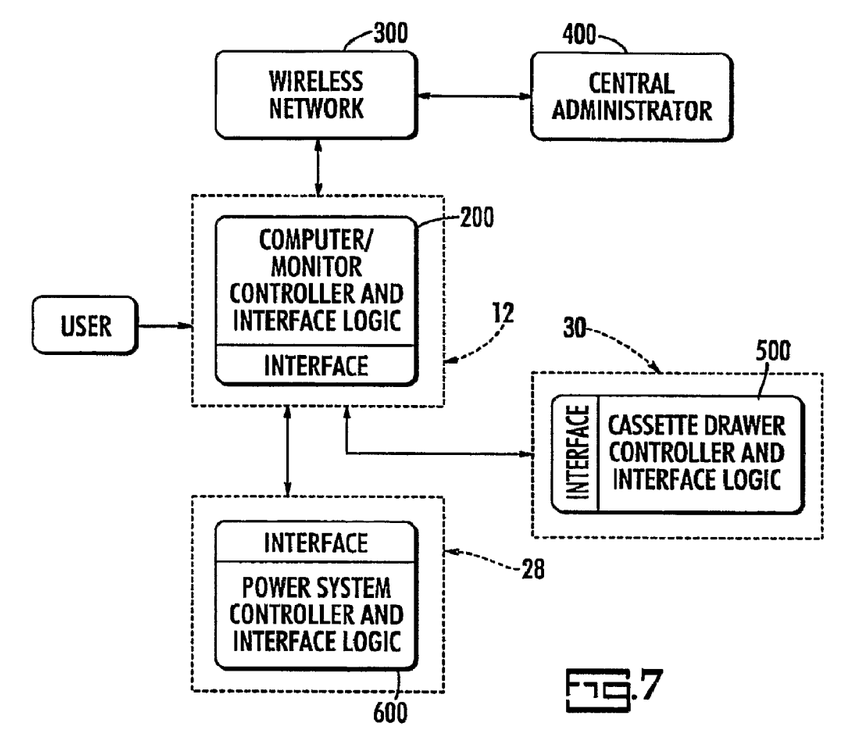
FIG. 7 is a block diagram of an operating system for a dispensing cart.

A block diagram of the operating system for the cart 10 is shown in FIG. 7. As illustrated, computer/monitor 12 includes a computer controller and interface logic 200 that receives computer controller input and generates computer controller output. For example, computer controller 200 process user input, such as the identity of user, the biometric information of user, pass codes entered by user. Furthermore, computer controller provides output to cassette drawer system 30 relating to the designation of cassette drawers included in the cassette drawer system 30. Significantly, computer/monitor 12 can, in real time, inventory medication as it is loaded and as it used, as well as which user is dispensing the medication. Additionally, computer/monitor 12 is equipped with a wireless network connection, preferably through SMTP (simple mail transfer protocol) so that the user of that cart 10 can communicate with a central administrator 400. Computer/monitor 12 also communicates with administrator 400 without the active assistance of the user. Accordingly, the status and whereabouts of the cart 10 can be constantly and effectively monitored through wireless communication.

As previously described, the cassette drawer system 30 also includes cassette drawer controller and interface logic 500. This cassette drawer controller receives input from the computer controller about the cassette drawers and their designations. Cassette drawer controller, therefore, can lock and unlock drawers based on this input. Furthermore, the cassette drawer controller logs what the drawers do, including when they are opened and by whom. Accordingly, the cassette drawer system 30 has the ability to monitor itself. Similarly, the power system 28 also includes controller and interface logic 600, which monitors the condition of battery 27, and controls the raising and lowering of the mast 24. For example, the condition of the battery 27 when low or when the unit is turning off due to low battery power, power system controller communicates these conditions to computer controller, which in turn reports by email to the administrator. Computer/monitor 12 will also automatically report by email an attempt to break into cart 10, a log of the charging system, a log of the times and the identities of users who have accessed each cassette drawer. Other information can also be reported.

Figure 8:
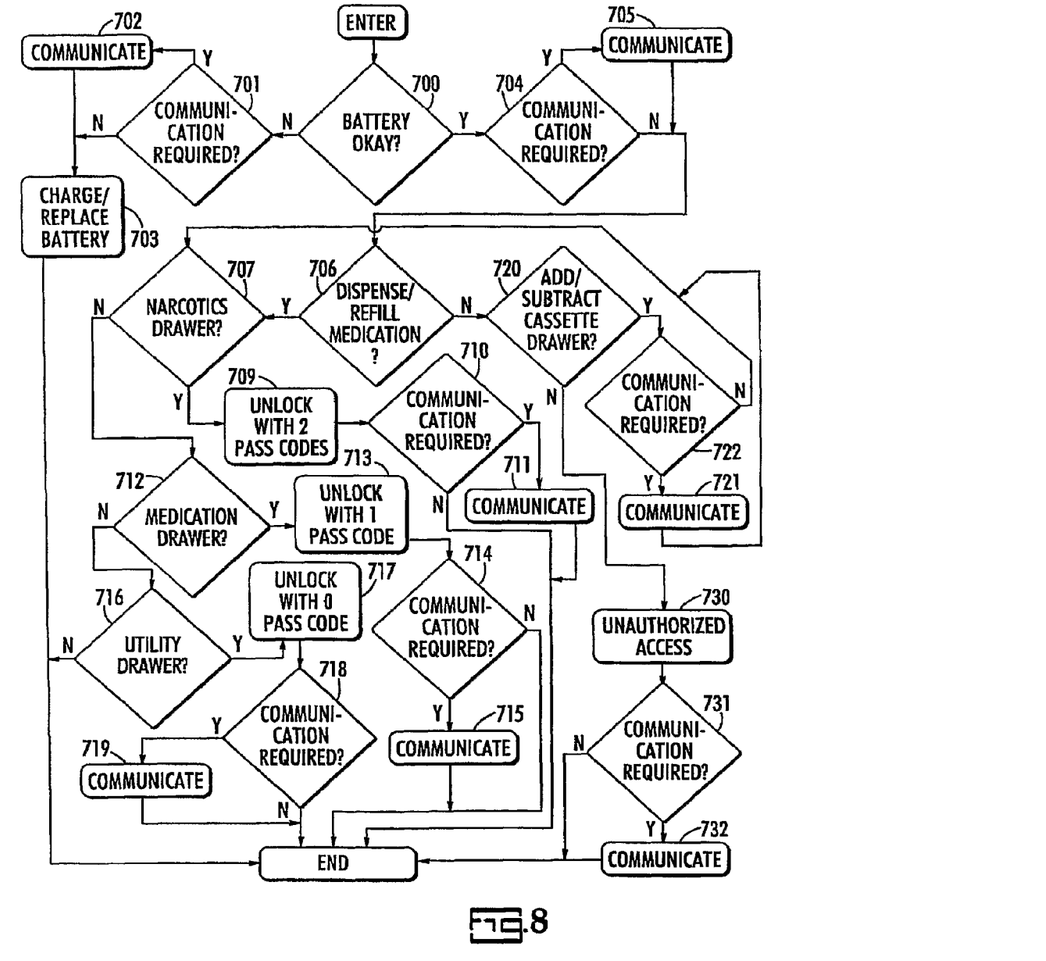
FIG. 8 is a flow chart illustrating the logic for medication cart system.

To summarize an embodiment of the logic for the medication cart system, FIG. 8 includes of flow chart. As shown, at 700, a decision is made by medication cart 10 whether the battery 27 is suitable. If the battery 27 is not in a good condition and if communication is required at 701 as to the status of the battery 27, an electronic communication is sent to central administrator at 702. If maintenance is needed, the battery 27 will be charged or replaced at 703. If the battery 27 is in good condition and communication is required at 704, an electronic communication is sent to central administrator at 705.

At 706, a decision is made as to whether medication must be dispensed or refilled. If narcotic medication must be dispensed or refilled at 707, the narcotics drawer is unlocked with two pass codes at 709. If communication as to the status of the narcotics drawer is required at 710, an electronic communication is sent to central administrator at 711. If non-narcotic medication must be dispensing or refilling at 712, the medication drawer is unlocked with on pass code at 713. If communication as to the status of the medication drawer is required at 714, an electronic communication is sent to central administrator at 715. If a utility drawer needs to be accessed at 716, the utility drawer is unlocked with no need for a pass code at 717. If communication as to the status of the utility drawer is required at 718, an electronic communication is sent to central administrator at 719.

If user adds or subtracts a cassette drawer from the cassette drawer system 30 at 720 and communication is required as to the status of the cassette drawer system 30 at 721, an electronic communication is sent to central administrator at 722. If, on the other hand, an unauthorized access to the cassette drawer system 30 is attempted or accomplished at 730, and communication is required as to the status of the cassette drawer system 30 at 731, an electronic communication is sent to central administrator at 732.

It is intended that the scope of the present invention include all modifications that incorporate its principal design features, and that the scope and limitations of the present invention are to be determined by the scope of the appended claims and their equivalents. It also should be understood, therefore, that the inventive concepts herein described are interchangeable and/or they can be used together in still other permutations of the present invention, and that other modifications and substitutions will be apparent to those skilled in the art from the foregoing description of the preferred embodiments without departing from the spirit or scope of the present invention.

What is claimed is:

1. An apparatus, comprising:
a medication dispensing cart having a computer with a computer monitor and a computer controller, a power system with a battery and a power system controller, and a cassette drawer system with a cassette drawer manager, a cassette drawer controller and a cassette drawer, wherein said computer controller, said power system controller, and said cassette drawer controller are interfaced with said medication dispensing cart, wherein said computer controller receives computer controller input and generates computer controller output, wherein said power system controller receives power system input and generates power system output, and wherein said cassette drawer controller receives cassette drawer input and generates cassette drawer output;
wherein said cassette drawer system is modularized, wherein said cassette drawer is a first cassette drawer, wherein said cassette drawer system includes a second cassette drawer, wherein the underside of said cassette drawer manager includes a first means for latching said first cassette drawer to said cassette drawer manager, and wherein the underside of said cassette drawer includes a second means for latching a second cassette drawer to said first cassette drawer.

2. The apparatus as recited in claim 1, further comprising: a work surface; a mast; and a base, wherein said computer and said work surface are carried by said mast, and wherein said mast is carried by said base.

3. The apparatus as recited in claim 2, wherein said power system is carried by said base.

4. The apparatus as recited in claim 2, wherein said cassette drawer manager is carried below said work surface.

5. The apparatus as recited in claim 2, wherein said base is a rolling base.

6. The apparatus recited in claim 2, wherein said computer monitor and said computer are one unit with said computer behind said computer monitor in the same housing.

7. The apparatus as recited in claim 2, wherein said work surface includes a slide out keyboard.

8. The apparatus as recited in claim 2, wherein said computer monitor is mounted to said mast using a tiltable bracket.

9. The apparatus as recited in claim 2, wherein the top side of said cassette drawer manager is bolted beneath said work surface.

10. The apparatus as recited in claim 2, wherein said power system controller input comprises at least one of height of said mast, status of said battery status, and weight of said computer and said work surface.

11. The apparatus as recited in claim 10, wherein said power system controller output comprises at least one of commands to said mast and status of said battery status.

12. The apparatus as recited in claim 1, wherein said computer controller input comprises at least one of user information, medication information, status of said cassette drawer system, and status of said power system.

13. The apparatus as recited in claim 12, wherein said user information comprises at least one of identity of user, a pass code, and location of user.

14. The apparatus as recited in claim 1, wherein said computer controller output comprises at least one of commands to said cassette drawer system and electronic messages relating to the status of said cassette drawer system, the status of said power system, and the location of said medication dispensing carts.

15. The apparatus as recited in claim 1, wherein said first latching means and said second latching means are the same and include a plurality of dovetail-shaped cutouts on the underside of said cassette drawer manager and the underside of said first cassette drawer, respectively, that correspond to a plurality of dovetail-shaped projections on the top side of said first cassette drawer and the top side of said second cassette drawer, respectively.

16. The apparatus as recited in claim 15, wherein said first latching means and said second latching means further include spring tabs having pins on the underside of said cassette drawer manager and the underside of said first cassette drawer, respectively, that correspond to recesses on the top side of said first cassette drawer and the top of said second cassette drawer, respectively.

17. The apparatus as recited in claim 1, wherein said second cassette drawer is a utility drawer having an electric lock controlled by said cassette drawer controller, wherein cassette drawer controller generates output to said electric lock when said utility drawer is connected to said cassette drawer system, and wherein said output is a command to remain unlocked when said utility drawer is latched to said first cassette drawer.

18. The apparatus as recited in claim 1, wherein said cassette drawer controller generates output to said computer controller when said second cassette drawer is connected to said first cassette drawer, wherein said output is a notification that said second drawer has been added to said cassette drawer system.

19. The apparatus as recited in claim 1, wherein said cassette drawer controller generates output to said computer controller when said second cassette drawer is disconnected from said first cassette drawer, and wherein said output is a notification that said second drawer has been removed from said cassette drawer system.

20. The apparatus as recited in claim 2, wherein said mast is vertically adjustable through means for adjusting.

21. The apparatus as recited in claim 20, wherein said power system controller includes a height actuator, and wherein said adjusting means is a button that is connected to electrical switch that is connected to said height actuator.

22. The apparatus as recited in claim 21, wherein said height actuator is connected to a weight sensor, wherein said weight sensor trips said height actuator if the weight of said work surface, said computer, and said computer monitor exceeds a preset, desired weight.

23. The apparatus as recited in claim 1, wherein said battery is connected to said medication dispensing cart using a "Y" electrical connector.

24. The apparatus as recited in claim 1, wherein said battery can be charged separately from said medication dispensing cart.

25. The apparatus as recited in claim 1, wherein said cassette drawer manager houses said cassette drawer controller, and wherein said cassette drawer controller monitors said cassette drawer.

26. The apparatus as recited in claim 1, wherein said cassette drawer includes a first compartment having a first lock and a first sensor, and a second compartment having second lock and a second sensor, wherein said second compartment contains narcotics, wherein said computer controller provides input to said cassette drawer controller about said first lock and said second lock, wherein said cassette drawer controller locks and unlocks said first lock and said second lock independently based on said input, and wherein said cassette drawer controller generates output to said computer controller about the status of said first lock and said second lock.

27. The apparatus as recited in claim 26, wherein said first sensor and said second sensor determine if said first compartment and said second compartment are open, closed, left open, or not fully closed, respectively, wherein said first sensor and said second sensor independently provide input to said cassette drawer controller, and wherein said cassette drawer controller generates output to said computer controller about the status of said first compartment and said second compartment.

28. The apparatus as recited in claim 26, wherein said cassette drawer controller requires a first pass code from said computer controller to unlock said first compartment, and wherein said cassette drawer controller requires a second pass code from said computer to unlock said second compartment.

29. The apparatus as recited in claim 1, wherein said computer is connected through a wireless communication link to a central administrator, wherein said computer includes an electronic mail system, and wherein said computer can automatically send electronic mail messages to said central administrator through SMTP about the status and whereabouts of said medication dispensing cart.

30. The apparatus as recited in claim 1, wherein said battery provides power to said medication dispensing cart sufficient to operate said cart for about 8 to about 10 hours.

31. An apparatus, comprising: a medication dispensing cart having a computer with a computer monitor and a computer controller, a power system with a battery and a power system controller, and a cassette drawer system with a cassette drawer manager, a cassette drawer controller and a cassette drawer, wherein said computer controller, said power system controller, and said cassette drawer controller are interfaced with said medication dispensing cart, wherein said computer controller receives computer controller input and generates computer controller output, wherein said power system controller receives power system input and generates power system output, and wherein said cassette drawer controller receives cassette drawer input and generates cassette drawer output;

wherein said mast is vertically adjustable through means for adjusting;

wherein said power system controller includes a height actuator, and wherein said adjusting means is a button that is connected to electrical switch that is connected to said height actuator; and wherein said height actuator is connected to a weight sensor, wherein said weight sensor trips said height actuator if the weight of said work surface, said computer, and said computer monitor exceeds a preset, desired weight.

32. An apparatus, comprising: a medication dispensing cart having a computer with a computer monitor and a computer controller, a power system with a battery and a power system controller, and a cassette drawer system with a cassette drawer manager, a base;

a mast extending vertically up from the base;

work surface disposed below the computer monitor and coupled to the mast;

wherein the cassette drawer manager is coupled to the work surface so as to be positioned beneath the work surface;

wherein the cassette drawer system further comprises a first drawer housing that is configured to be removably coupled beneath the cassette drawer manager, wherein the first drawer housing defines an interior;

at least one pull-out drawer disposed in the interior; and a second drawer housing that is configured to be removably coupled beneath the first drawer housing and to hold another pull-out drawer.

33. An apparatus, comprising: a medication dispensing cart having a computer with a computer monitor and a computer controller, a power system with a battery and a power system controller, and a cassette drawer system with a cassette drawer manager, a base;

a mast extending vertically up from the base;

work surface disposed below the computer monitor and coupled to the mast;

wherein the cassette drawer manager is coupled to the work surface so as to be positioned beneath the work surface;

a drawer housing having a front, a back and sides, wherein the front defines an opening and wherein the back includes a recess through which the mast vertically passes when the drawer housing is removably coupled to the cassette drawer manager; and at least a first pull-out drawer held within the opening of the drawer housing.

34. An apparatus as in claim 33, wherein the drawer housing defines a pair of openings that are positioned on opposing sides of the mast, and wherein a pull-out drawer is disposed in each opening.

35. An apparatus as in claim 33, wherein the drawer housing is a first drawer housing further comprising a second drawer housing removably coupled beneath the first drawer housing.

36. An apparatus as in claim 33, wherein the mast is a single mast.

* * * * *